United States Patent
Frank et al.

(10) Patent No.: US 7,327,452 B2
(45) Date of Patent: Feb. 5, 2008

(54) LIGHT BEAM APPARATUS AND METHOD FOR ORTHOGONAL ALIGNMENT OF SPECIMEN

(75) Inventors: Jonathan Frank, Los Gatos, CA (US); Daniel Cotton, Walnut Creek, CA (US)

(73) Assignee: Credence Systems Corporation, Milpitas, CA (US)

( * ) Notice: Subject to any disclaimer, the term of this patent is extended or adjusted under 35 U.S.C. 154(b) by 409 days.

(21) Appl. No.: 10/912,896

(22) Filed: Aug. 9, 2004

(65) Prior Publication Data

US 2006/0028641 A1  Feb. 9, 2006

(51) Int. Cl.
G01N 21/01 (2006.01)
G01N 21/55 (2006.01)
G01B 9/00 (2006.01)

(52) U.S. Cl. .................. 356/244; 356/124; 356/445
(58) Field of Classification Search .............. None
See application file for complete search history.

(56) References Cited

U.S. PATENT DOCUMENTS

| | | | |
|---|---|---|---|
| 3,470,377 A * | 9/1969 | Kuehne et al. ............ 250/204 |
| 3,524,694 A | 8/1970 | Kelin |
| 3,711,186 A | 1/1973 | O'Connor |
| 3,782,827 A * | 1/1974 | Nisenson et al. .......... 356/600 |
| 3,912,378 A | 10/1975 | Goto |
| 4,634,234 A | 1/1987 | Baumann |
| 5,004,307 A * | 4/1991 | Kino et al. ................ 359/356 |
| 5,208,648 A | 5/1993 | Batchelder et al. |
| 5,220,403 A | 6/1993 | Batchelder et al. |
| 5,276,545 A * | 1/1994 | Daun et al. ............... 359/198 |
| 5,282,088 A | 1/1994 | Davidson |
| 5,461,472 A * | 10/1995 | Harvey et al. ............ 356/138 |
| 5,475,316 A | 12/1995 | Hurley et al. |
| 5,940,545 A | 8/1999 | Kash et al. |
| 6,252,412 B1 | 6/2001 | Talbot et al. |
| 6,462,814 B1 | 10/2002 | Lo |
| 6,509,750 B1 | 1/2003 | Talbot et al. |
| 6,591,121 B1 | 7/2003 | Madarasz |
| 6,594,006 B1 * | 7/2003 | Muehlhoff et al. ...... 356/139.03 |
| 6,618,120 B2 * | 9/2003 | Ueta ........................ 355/72 |
| 6,621,275 B2 * | 9/2003 | Cotton et al. ............ 324/537 |
| 2002/0113973 A1 * | 8/2002 | Ge ........................... 356/510 |
| 2003/0071981 A1 * | 4/2003 | Ueta ........................ 355/72 |
| 2003/0098692 A1 * | 5/2003 | Cotton et al. ............ 324/537 |
| 2003/0220760 A1 * | 11/2003 | Kasapi ...................... 702/120 |
| 2004/0016728 A1 * | 1/2004 | Liu et al. ................. 219/121.71 |
| 2006/0176477 A1 * | 8/2006 | Frank et al. .............. 356/244 |

OTHER PUBLICATIONS

Optical Tooling for Precise Manufacturing and Alignment, Philip Kissam, p. 103-107, McGraw-Hill, 1962, TA 165.K53.*

* cited by examiner

Primary Examiner—Gregory J. Toatley, Jr.
Assistant Examiner—Jonathan Skovholt
(74) Attorney, Agent, or Firm—Sughrue Mion, PLLC; Joseph Bach (57) ABSTRACT

A system for orthogonal alignment of a specimen disclosed. The system includes a light-beam illumination source, collection optics, imaging optics, and a tiltable specimen holder. The light-beam source is activated to illuminate a spot on the specimen, and the imaging optics is used image that spot. The location of the spot on the imager is used to determine whether the specimen is orthogonal to the optical axis of the collection optics.

27 Claims, 7 Drawing Sheets

LIGHT BEAM APPARATUS AND METHOD FOR ORTHOGONAL ALIGNMENT OF SPECIMEN

BACKGROUND OF THE INVENTION

1. Field of the Invention

The present invention relates to a system for leveling a specimen, such as a substrate, to be orthogonal to the optical axis of an imaging system.

2. Description of the Related Art

Figure 1A:
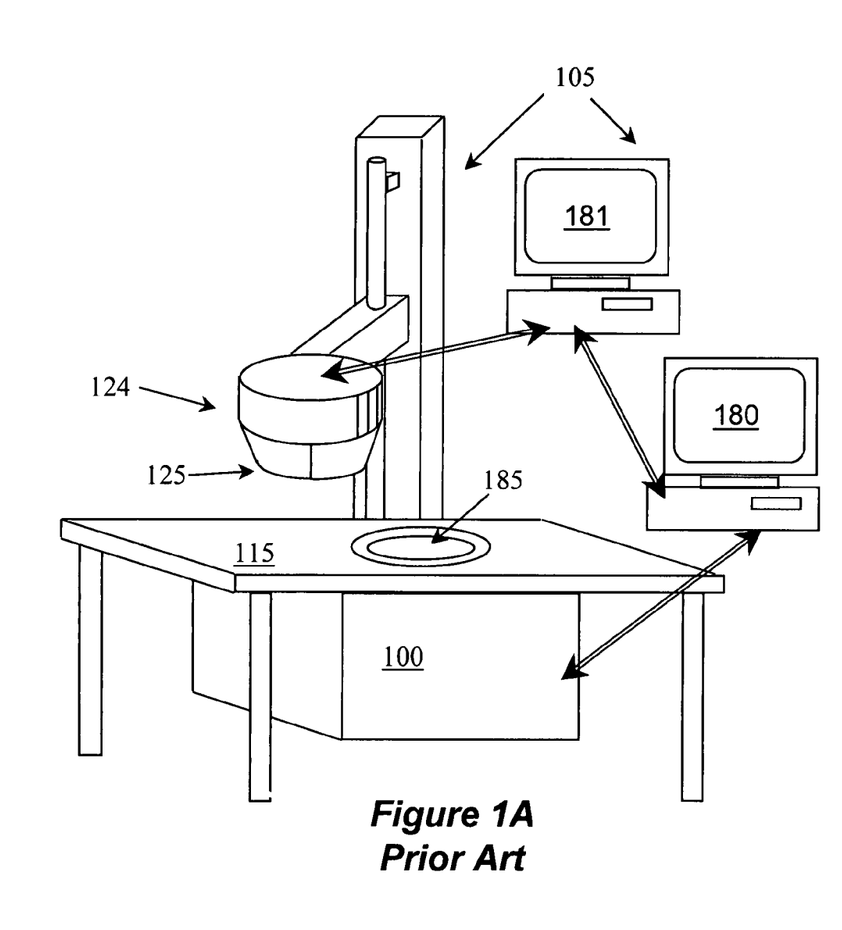
FIGS. 1A and 1B are general schematics depicting the major components of the testing and debug system according to the prior art.
Figure 1B:
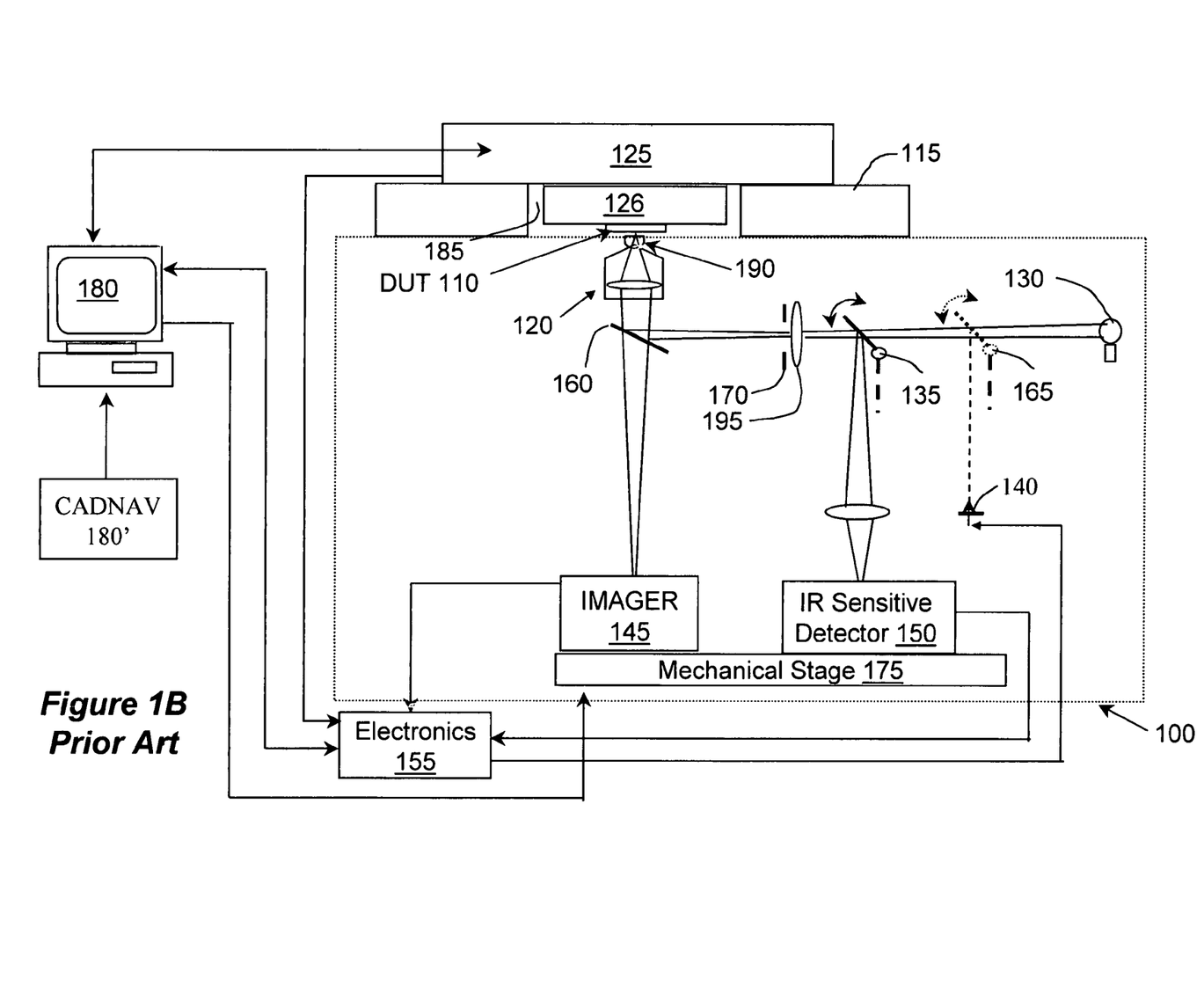

Many optical systems for inspection of specimen, such as substrates, exist in the prior art. One such system is described in U.S. Pat. No. 6,621,275, which is assigned to the current assignee and which is incorporated herein by reference in its entirety. Such systems can be used for inspection or testing and debug of semiconductor substrates or integrated circuits. Examples of systems for imaging flip-chip type integrated circuits through the silicon substrate are described in U.S. Pat. Nos. 5,208,648, 5,220,403 and 5,940,545. FIGS. 1A and 1B depict an example of an integrated-circuit testing system that is helpful for the understanding of the present invention.

FIGS. 1A and 1B are general schematics depicting the major components of the testing and debug system according to the prior art. The system operates in conjunction with a commercially available automated testing equipment 105 (ATE). The ATE generally comprises a controller, such as a pre-programmed computer 181, and a test head 124, which comprises an adapter 125 used to deliver signals generated by the controller 181 to the device under test (DUT) 110 (FIG. 1B) in a manner well known in the art. Specifically, the ATE is used to generate signals that stimulate the DUT to perform various tasks, as designed by the chip designer to check and/or debug the chip. The various signals generated by the controller 181 are delivered to the DUT via the adapter 125. The adapter 125 may include a space transformer, a DUT load board 126 and a DUT socket, in a manner well known in the art.

In the embodiment depicted in FIGS. 1A and 1B, the ATE test head is placed on top of a vibration isolated test bench 115, while the chamber 100 that houses the entire optics, imaging and sensing system, and an X-Y-Z stage 175, is situated below. The ATE is used to place the DUT from above, so that it is visible to the optics 120 (including an objective, that is not shown) via opening 185. Stage 175 enables placing of the collecting optics 120 at any locations within the opening 185.

The various elements of the system of FIGS. 1A and 1B will now be described with reference to their operational modes. Generally, the system operates in two modes: navigation mode and detection mode. In the navigation mode, switchable mirrors 135 and 165 are placed out of the optical path, as shown by the broken lines in FIG. 1B, so that the illumination source 130 illuminates the DUT 110. The light that reflects back from the DUT 110 is passed through the beam splitter 160 and onto the imager 145. The imager 145 can be any two-dimensional detector capable of imaging the DUT 110, such as, for example, vidicon camera, or a InGaAs focal plane array. In this manner, an image of the DUT is acquired.

A mechanized aperture 170 is provided at the image plane of the collection optics 120, together with field lens 195. In this particular example the entrance pupil of collection optics 120 is imaged by the field lens 195 onto the entranced plane of the focusing element of the detector in imager 145. In one implementation (not depicted here) the pupil entrance of the collection optics is imaged by the focusing element onto a fiber-optics which couples the collected photons into the detector in imager 145. According to this feature, the illumination path takes place through the mechanized aperture 170 (which is positioned at the image plane of the collection optics) and thereby its opening defines the field-of-view on the sample or device under test. The aperture also defines the portions of the sample imaged onto the imager 145. That is, depending on the particular test to be run, one may wish to select any particular section of the DUT for emission. Using information about the chip design and layout stored in CAD software, such as, for example, Cadence, and using navigation software, such as, for example, Merlin's Framework available from Knights Technology, one may select a particular device for emission test, and block the image and emission of the other devices in the field-of-view of the collection optics. When the user selects a device or location, the system activates the stage 175 so that the collection optics is centered on the selected device or location. Alternatively, as long as the area of interest is in the field-of-view of the collection optics, one can isolate the area of interest with the apertures and proceed to image and detect "selectively". Then, the aperture 170 may be adjusted to increase or decrease the field of view as appropriate for the particular test desired.

When an appropriate field of view has been set and an image obtained, mirror 135 is rotated so that the light path towards the IR sensitive detector 150 is established (opened), as depicted by the solid line drawing. Additionally, light source 130 is shut off or blocked during testing. It should be appreciated, of course, that chamber 100 prevents any external light from reaching any of the optics, imagers and sensors enclosed within.

Photon sensing during testing is done by detector 150, which is, for example, an infrared sensor, such as a photomultiplier tube (PMT), a photocathode coupled to a multi-channel plate (MCP), an avalanche photodiode (APD), etc. In this configuration the ATE is sending testing signals to the DUT and, as the various devices inside the DUT switch state they emit light. The light is collected by optics 120 and is directed to the photodetector 150, which converts the optical input into an electrical output signal. The output signal from the detector 150 is sampled by the high-speed data acquisition electronics 155. Controller 180, which may be a general-purpose computer running dedicated software, is used to control the various elements of the system, such as the actuators and stages and sampler. The controller 180 receives sync signals from the ATE 105.

Another optional feature described in the prior art is the use of a laser illumination of the DUT. The laser feature can be used as a "laser pointer" to allow pointing to a device of interest. During navigation, light source 130 is activated and mirror 135 is swung out of the optical path position (dashed line), so as to illuminate the DUT. Light reflected from the DUT is then passed through the half mirror 160 and is imaged by the imager 145. Once an image of an area of interest on the DUT is obtained, minor 165 is swung into the optical path position. Then, laser source 140 is activated to create a laser beam and illuminate the DUT. Laser light reflected from the DUT is imaged as a relatively small "laser pointer" image by the imager 145. The stage can then be actuated and moved until the "laser pointer" points to a device of interest. Once that is achieved, laser source 140 is turned off and mirror 135 is swung into the optical path (solid-line) position. In this position, the optical path to detector 150 is aligned onto the same device previously illuminated by the "laser pointer" so that it can be emission tested.

Also shown in FIG. 1B is a solid immersion lens (SIL) 190, being part of the optics 120. The optics 120 includes an objective lens (not shown) which is housed in an objective housing. The use of a SIL enables a more efficient collection of photons, especially in conditions where the emission is very faint. When using a SIL, it is a normal practice to place the SIL in physical contact with the object to be inspected.

The system depicted in FIGS. 1A and 1B and described above is provided as an example of an optical inspection and/or testing system so that a better understanding of the invention can be had. However, it should be appreciated that optical systems of other designs can be improved using the invention described and claimed herein.

SUMMARY OF THE INVENTION

The present inventors provide an apparatus and method for leveling of a specimen to be inspected using an optical testing tool.

In one aspect of the invention, a bench is provided for placing the specimen thereupon. The bench includes mechanized lifters so that the lifters can be controlled to change the level position of the specimen. While in one embodiment the lifters are controlled manually, in another embodiment the mechanized lifters are controlled by the system's controller. A laser is used to sample the specimen and an imager is used to image the laser beam reflecting from the specimen. The location of the laser beam spot on the imager is used to determine the level positioning of the specimen.

BRIEF DESCRIPTION OF THE DRAWINGS

FIG. 8 is another embodiment of the inventive system, while

The invention is described herein with reference to particular embodiments thereof, which are exemplified in the drawings. It should be understood, however, that the various embodiments depicted in the drawings are only exemplary and may not limit the invention as defined in the appended claims.

DETAILED DESCRIPTION

An embodiment of the invention will now be described in details with reference to FIG. 2 and, for illustration purposes, it will be depicted as implemented in the system of FIGS. 1A and 1B. Such a system is particularly useful for emission testing of integrated circuits. Since emission from integrated circuits is very faint, the system described with respect to FIG. 2 uses a SIL. However, those skilled in the art can readily observe that the invention can be easily implemented in other optical systems.

When working with optical testing equipment, such as the one depicted in FIGS. 1A and 1B, the present inventors noted that sometimes the light collection efficiency drops, even when every part of the system appears to be in good working order. Such degradation was observed even when a SIL was used in the collection optics. The inventors have investigated the root cause for this unexplained degradation of light collection. The investigation revealed that when the area observed is not level or perpendicular to the optical axis of the collection optics or the SIL, light collection efficiency degrades. The term "level," as used herein and throughout the specification and claims, will be used to mean an orientation that is perpendicular to the optical axis of the collection optics or SIL. The term "orthogonal," meaning intersecting or lying at right angles. will sometimes be used to refer to the perpendiculars, or "level" orientation of the area observed with regard to the collection optics or SIL.

Figure 2:
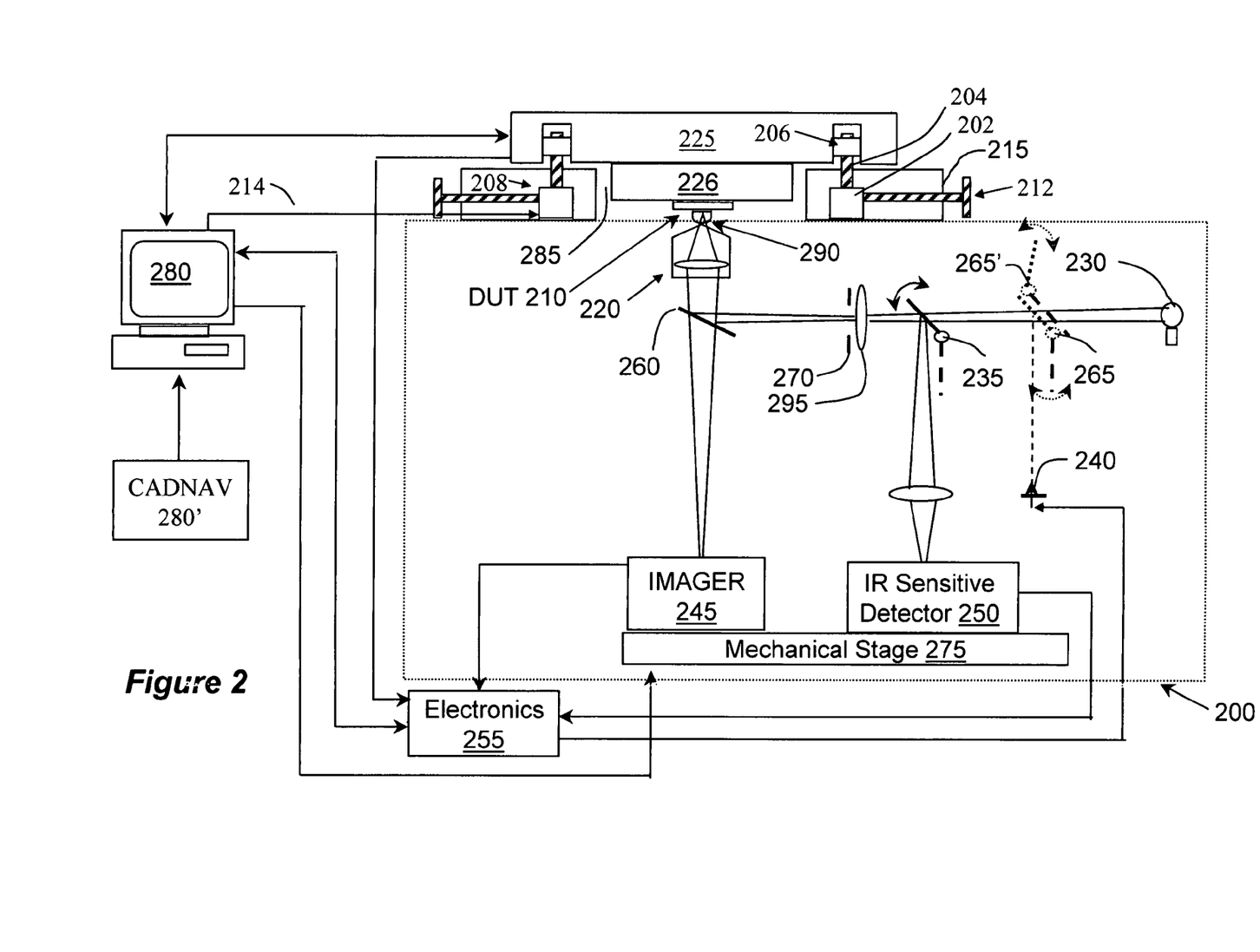
FIG. 2 depicts an embodiment of the invention as implemented in the system of FIGS. 1A and 1B.

In FIG. 2, elements corresponding to those depicted in FIGS. 1A and 1B are designated by similar characters, except that in FIG. 2 these characters are in the 200 range. In this particular example, the optical system is used for investigating light emission from integrated circuits IC's). In many of the examples discussed below, the system may be sometimes used without the objective or the SW of collection optics 220. Accordingly, to take full advantage of the various embodiments described, the collection optics 220 may be provided in the form of a turret having multiple optical elements, such as conventional turrets used in microscopes with various magnifications. However, one location of the turret should remain empty to implement an optical path without an objective and/or SIL.

As can be seen, the system of FIG. 2 includes a bench 215, in which mechanized lifters 208 are fitted. While due to the two-dimensional nature of the drawings only two lifters 208 are shown, a better effect can be achieved when three or four lifters are used. In this example, two different implementations of the lifters 208 are illustrated. According to one implementation, the lifters are controlled mechanically (i.e., manually), while according to a second implementation, the lifters are controlled electrically (i.e., user or computerized automatic feedback control). The invention can be easily implemented using either type of lifters or, alternatively, a lifter having electrical control and manual fine-tuning control may also be used.

Each mechanize lifter includes a housing 202 and a screw-type shaft 204. In the case of a mechanically controlled lifter, the housing 202 houses gears which translate the rotation of tuning knob 212 into the rotation of shaft 204. In the case of electrically controlled lifters the housing houses an electrical motor that received electrical signals (shown by arrow 214) and rotates the shaft 204 accordingly. The motors may be electrical motors, such as servo or stepper motors, and each motor is controlled independently by the controller 280. The controller may generate the control signals according to a user's input, or it may generate the signal automatically according to a feedback algorithm.

A threaded sleeve 206 rides on the shaft 204, so that as the motor rotates the shaft the sleeve 206 goes up or down on the shaft 204—depending on the rotation direction of the motor 202. As the sleeve 206 goes up or down, it changes the elevation of the ATE adapter 225, thereby changing the level orientation of the DUT 210. In this manner the adapter 225 is made into a tiltable holder for the DUT 210.

Figure 3A:
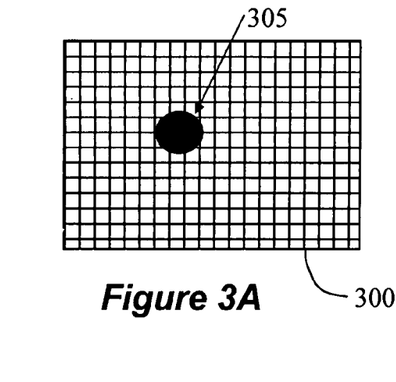
FIGS. 3A and 3B depict an illustration of a laser spot imaging at two testing locations or testing of two different specimen.

The leveling of the DUT 210 according to an embodiment of the invention will now be described with reference to FIGS. 3A, 3B, 4A, and 4B. The system is calibrated using a DUT or other sample which is know to be flat and have no undulations or surface features. Alternatively, a sample may be used which has one section thereof that is flat and lacks any surface or topographical features. The sample is mounted onto adapter 225, optionally using a load board 226, and is mechanically tested to be level using conventional techniques for verifying leveling of an object. Mirror 265 is then placed out of the optical path and light source 230 is turned on so as to illuminate a flat area of the calibration sample. Additionally, the SIL, if used, may be removed from the optical path. The imager images the illuminated area of the sample, and the intensity of the imaged light is recorded. The lifters 208 are then operated to perturb the leveling of the sample to one direction and another image is acquired and its light intensity recorded. If the light intensity is below the first recorded intensity, then the first setting is considered to be superior to the perturbed position. The sample may then be perturbed to a different direction, e.g., orthogonal to the first perturbation, and another measurement is taken. On the other hand, if the intensity of the image from the perturbed sample is higher, it is determined that the perturbed position is superior to the original setting. The lifters may then be operated to investigate whether further tilting in that direction is required to level the sample even further. The setting with the highest intensity in all tilt directions is defined as the calibrated leveled setting. When this position is achieved, mirror 265 is swung into the optical path, light source 230 is turned off, and laser 240 is turned on. Additionally, the objective (part of optics 220) and field lens 295 may be moved out of the optical path. In this condition, the location of the reflected laser spot on imager 245 is defined as the calibrated level location, as shown in FIG. 3A. In FIG. 3A the reflected laser spot 305 is shown as illuminated on the two-dimensional array 300.

Figure 5:
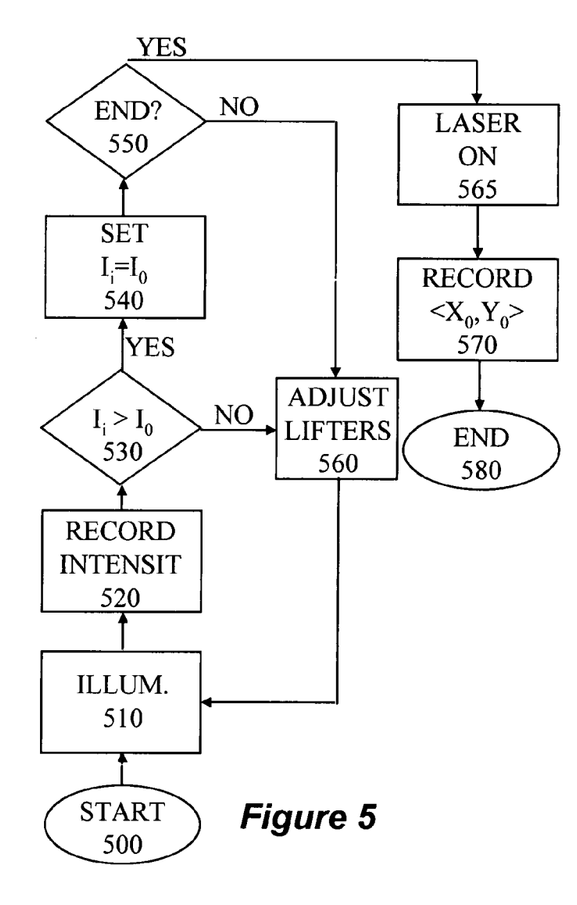
FIG. 5 is a block diagram of a calibration process according to an embodiment of the invention.

FIG. 5 is a block diagram depicting a method which can be implemented either manually or automatically using a computer/controller that is programmed to execute the method as described. The method begins at 500, in which the appropriate optical path is established and the initial leveling is confirmed by a conventional external method (mechanical leveling). In the embodiment of FIG. 2, mirrors 235 and 265 are taken out of the optical path. Light source 230 is energized to illuminate the DUT (step 510). The reflected intensity $I_i$ on imager 245 is recorded (520) and is compared to a reference intensity $I_0$ (530). On initial calibration, the reference intensity may be set to the initial intensity level, set to zero, or set to some predetermined value that is the minimal threshold needed to perform adequate inspection and testing of the DUT. When the reference intensity is set to the initial intensity, step 530 may be skipped and the process may proceed to step 560. Setting a minimal threshold value can be done by, for example, by determining that the reflected intensity is within a defined range of the illumination intensity. That is, the theoretical value that one can hope to achieve is a reflected intensity that is equal to the illumination intensity. If one determine that, say, 2% loses are expected and are acceptable, then a measured intensity that is 2% below the illumination intensity is proper and can be used as an upper threshold intensity level.

In step 530, if the recorded intensity is below the reference intensity, the process proceeds to step 560, and the lifters are adjusted to better level the DUT. Then the process returns to step 510 for another iteration. On the other hand, if at step 530 the recorded intensity $I_i$ is above the reference intensity $I_0$, the recorded intensity $I_i$ is set as the new reference intensity $I_0$. A determination is then made as to whether to perform another iteration or to end the calibration process. When further iteration is required, the process proceeds to step 560 for another iteration. When no further calibration is necessary, the process proceeds to step 565 wherein the light source is turned off, the appropriate mirrors are swung into place (mirror 265 in FIG. 2) and the laser is energized to illuminate the sample. Additionally, the objective may be removed from the optical path. In step 570 the location of the laser spot reflection on the imager is recorded, for example, in an $<X_0,Y_0>$ format (see spot 305 in FIG. 3A), wherein the leveling process ends at step 580.

After calibration, when a test sample is placed in the system, it is illuminated by the laser and the reflection spot's location is noted. In this respect, optionally mirror 265' is provided in the form of a half mirror, so that it allows light from light source 230 to pass therethrough and also illuminate the DUT. In this manner, the imager 245 provides an image of both the DUT's surface and the laser spot. This allows one to level the DUT and also to determine the spot's location with respect to the DUT's topography. If mirror 265 is a solid mirror, the reflected laser light will show up on imager 245 in a certain location illuminating one or more pixels, while the remaining pixels will remain dark. This is the situation depicted in FIG. 3A. Of course, one may use both a solid mirror and a half mirror, e.g., mirror 265 being solid, while mirror 265' being half mirror.

Figure 3B:
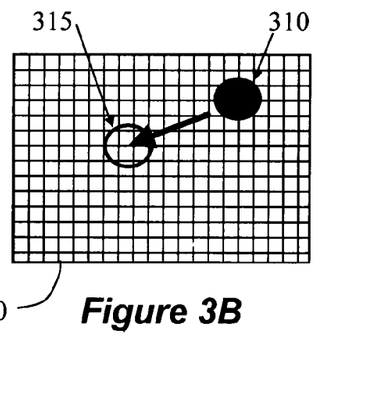

If the reflected laser spot is not in the same location as the calibrated location, the lifters are activated to change the leveling until the spot appears in the same location as the calibrated location. This is illustrated in FIG. 3B, i.e., the current reflection spot's location is depicted as solid circle 310, and the calibrated location is depicted as hollow circle 315. As depicted by the arrow, the lifters are operated so as to move the spot 310 until it overlaps spot 315.

Figure 6:
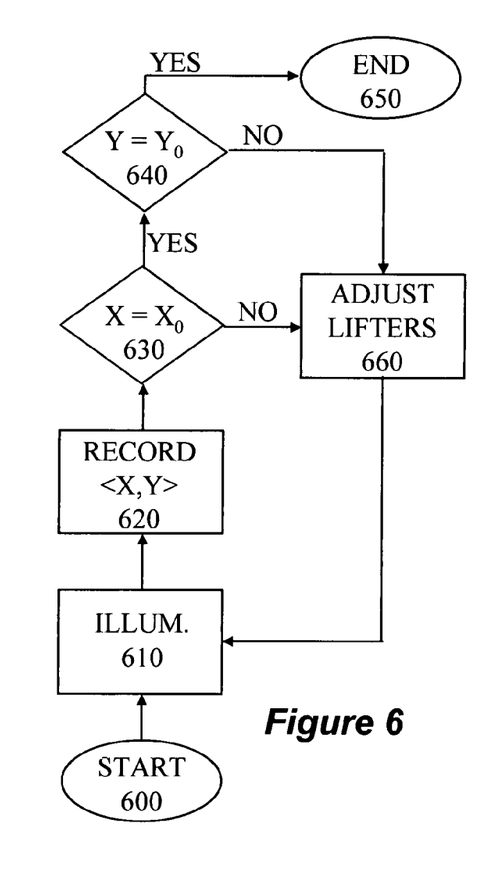
FIG. 6 is a block diagram of a leveling process according to an embodiment of the invention.

FIG. 6 depicts a method which can be implemented either manually or automatically using a computer/controller that is programmed to execute the method for leveling as described. The method begins at 600, in which the appropriate light path is established by positioning the appropriate mirrors in the appropriate position. The DUT is then illuminated at step 610 and the <X,Y> position of the spot on the two-dimensional imager 245 is recorded at step 620. At step 630 the recorded X position is compared to the reference $X_0$ position. If the X position doesn't match, or is not within an acceptable range of reference $X_0$ position the process proceeds to step 660 to adjust the lifters and perform another iteration via step 610. On the other hand, if the X position is proper, the process proceeds to step 640 to compare the recorded Y position to the reference $Y_0$ position doesn't match, or is not within an acceptable range of reference $Y_0$ position, the process proceeds to step 660 to adjust the lifters and perform another iteration via step 610. If the Y position is proper, the process ends at step 650.

Figure 4A:
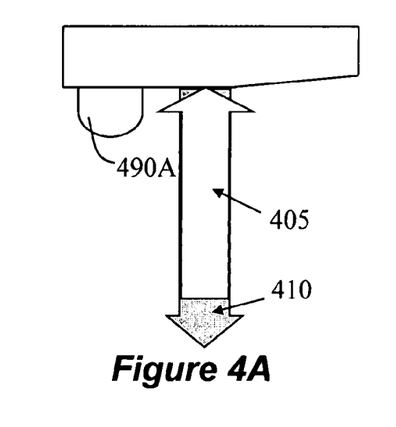
FIGS. 4A and 4B depict an illustration of a laser spot illumination at two testing locations on a specimen or of two different specimen.

The mechanism behind the leveling operation can be explained with reference to FIGS. 4A and 4B. That is, when the laser beam 405 illuminates a flat area that is level, i.e., orthogonal to the optical axis, the reflected laser beam 410 follows the same path as the illumination laser beam, as depicted in FIG. 4A. However, when the laser beam 405 illuminates an area that is not flat or not level, the reflected light beam 410 follows a different path from the illumination light beam, as depicted in FIG. 4B.

Figure 4B:
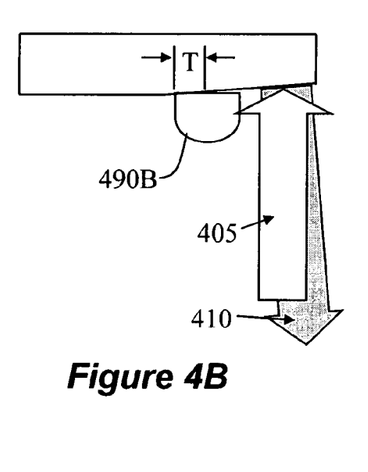

FIGS. 4A and 4B also demonstrate why this problem is particularly important to detect when a solid immersion lens (SIL) is used as part of the optical elements of the system. Notably, as is known in the art, when a SIL is used, the SIL is made to come in contact with the specimen to obtain improved light collection efficiency. When the area to be inspected is orthogonal to the optical axis, the SIL can be properly place on the flat area to achieve full coupling of light, as shown in FIG. 4A. On the other hand, when the area to be inspected is not orthogonal to the optical axis, the SIL can not be properly placed on the specimen and the collection surface of the SIL will not be in full contact with the specimen, as shown in FIG. 4B. That is, the SIL's contact area with the DUT is depicted as T, and it's the only area that collects reflected light. Consequently, light collection efficiency is degraded, as was observed by the current inventors. However, using this invention the user can determine whether the area to be inspected is orthogonal to the optical axis before placing the SIL on the specimen. If the area is not orthogonal, the inventive system can be used to tilt the specimen so as to place the area to be inspected in an orthogonal relationship to the optical axis. This ensures that when the SIL is landed on the specimen, it will form full contact and light collection efficiency will be high.

As can be understood, the inventive system and alignment procedure can be used anytime the bench is not aligned, the specimen itself has a sloped surface, or-the topography of the specimen is such that some areas are not flat. Therefore, in some cases, e.g., when the bench itself is not aligned or the specimen has a sloped surface, the alignment procedure can be performed only once for each specimen. On the other hand, when the specimen has a varying surface topography, the alignment procedure should be repeated for each area of the specimen to be inspected.

Figure 7:
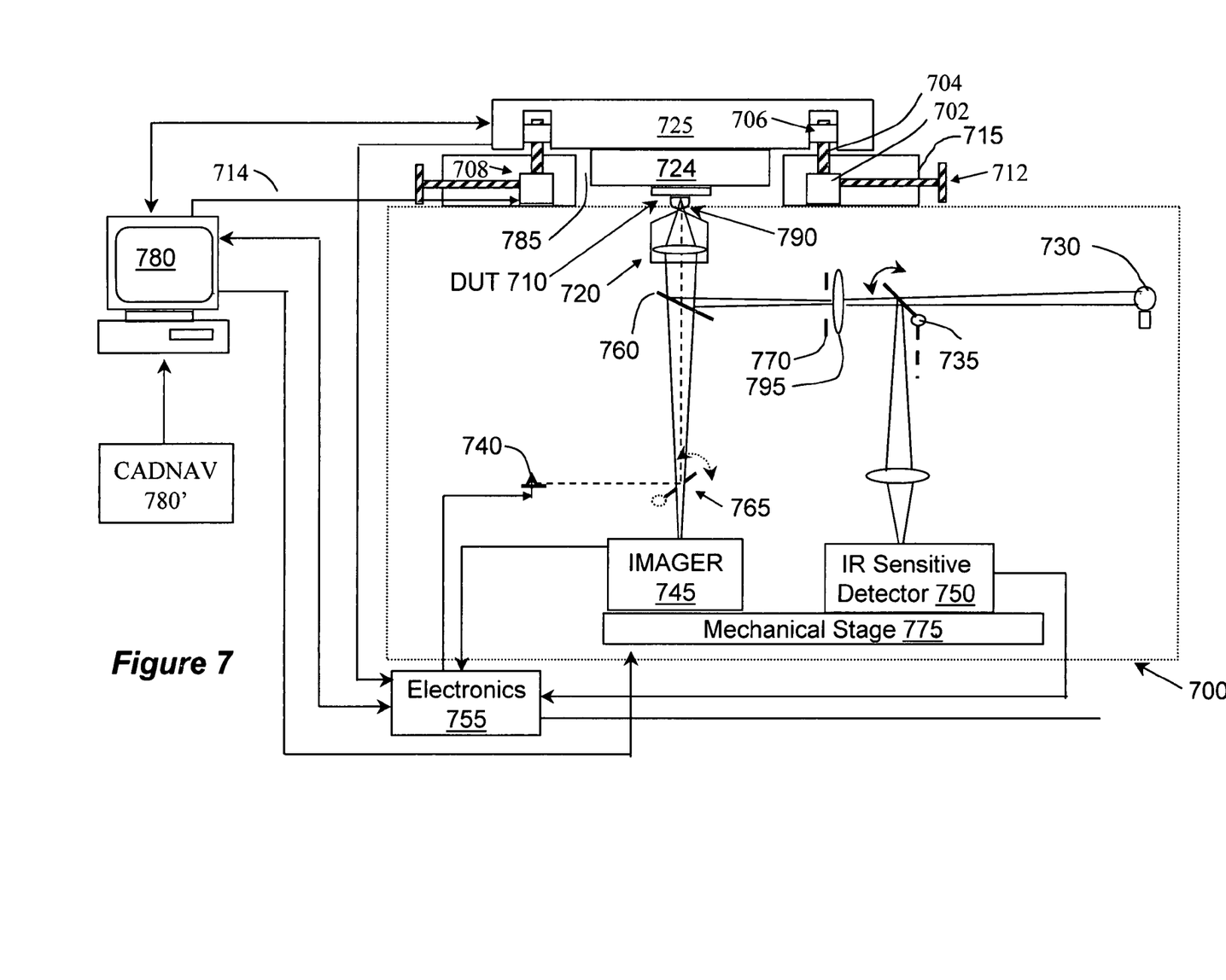
FIG. 7 is an embodiment that is a modification of the embodiment of FIG. 2.

FIG. 7 depicts another embodiment, which is a variation of the embodiment of FIG. 2. Elements in FIG. 7 that are similar to elements in FIG. 2 have the same designation, except in the 700's range. In FIG. 7 a different optical path is provided for the laser 740. Rather than being in the same optical path as the light source 730, the laser 740's optical path is provided independently and is coupled to the same optical path of the imager 745 using mirror 765. In this case, mirror 765 is a half mirror that reflects the illumination laser beam towards the DUT, but allows the reflected laser beam to pass into the imager 745. As explained above, during calibration and leveling procedure, the objective (collection optics 720) may be removed from the optical path.

Figure 8:
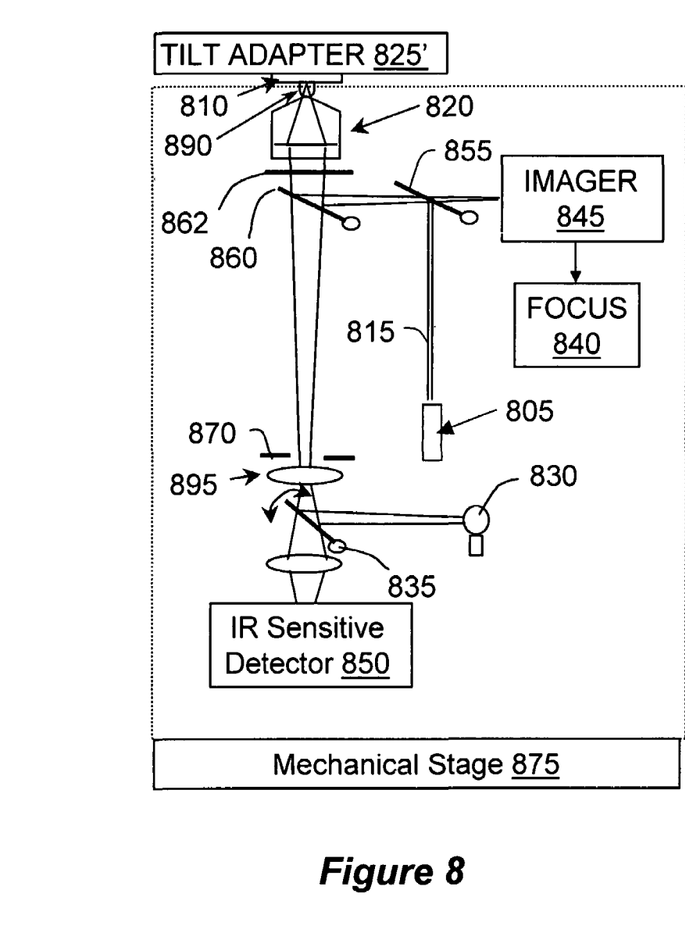

Yet another embodiment is depicted in FIG. 8. In this embodiment, the IR detector 850 is provided a direct "line of sight" to the specimen 810, which is mounted to a tiltable adapter 825. Collection optics 820 may or may not include SIL 890. All illuminations, i.e., light source 830 and laser 805, are provided from outside of the line of sight, and is introduced onto the DUT via insertable mirrors 835, 855 and 860. As in the embodiments of FIGS. 2 and 7, lens 895 and mechanical slit 870 may be provided in order to delineate a field of view for the system. Focus 840 may be an intensity measurement routine as described above.

Figure 9:
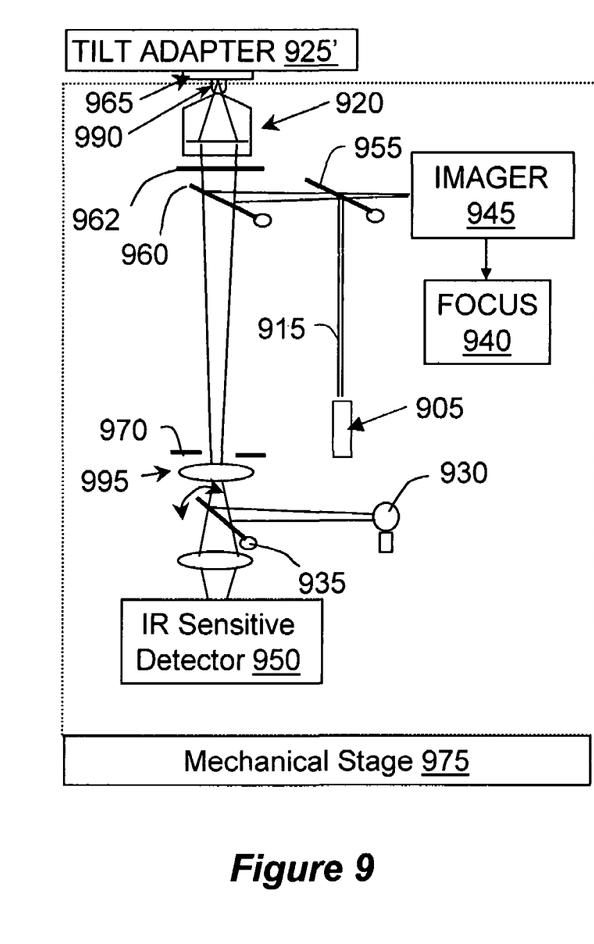
FIG. 9 is the embodiment of FIG. 8 in a setup suitable for calibration.
Figure 10A:
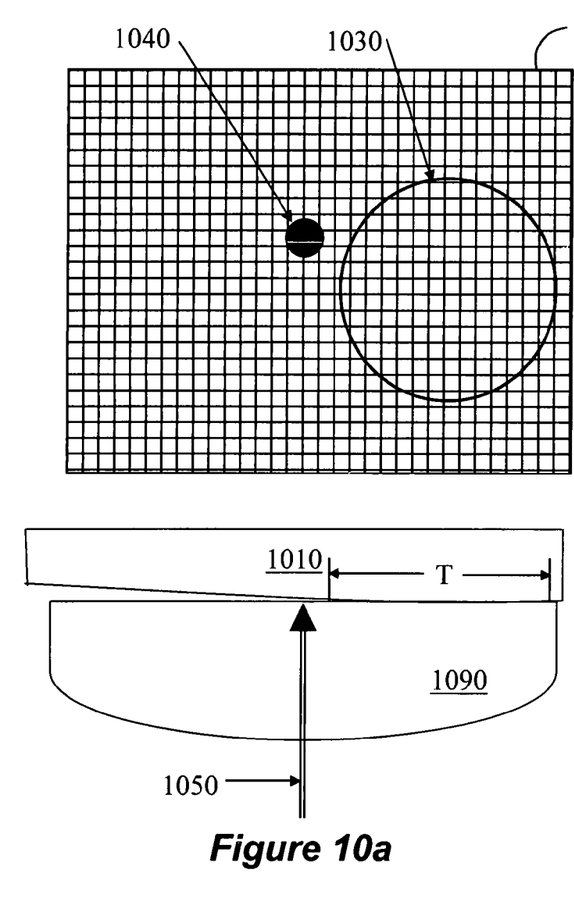
FIGS. 10a and 10b are schematic depicting an alignment process using the setup of FIG. 9.
Figure 10B:
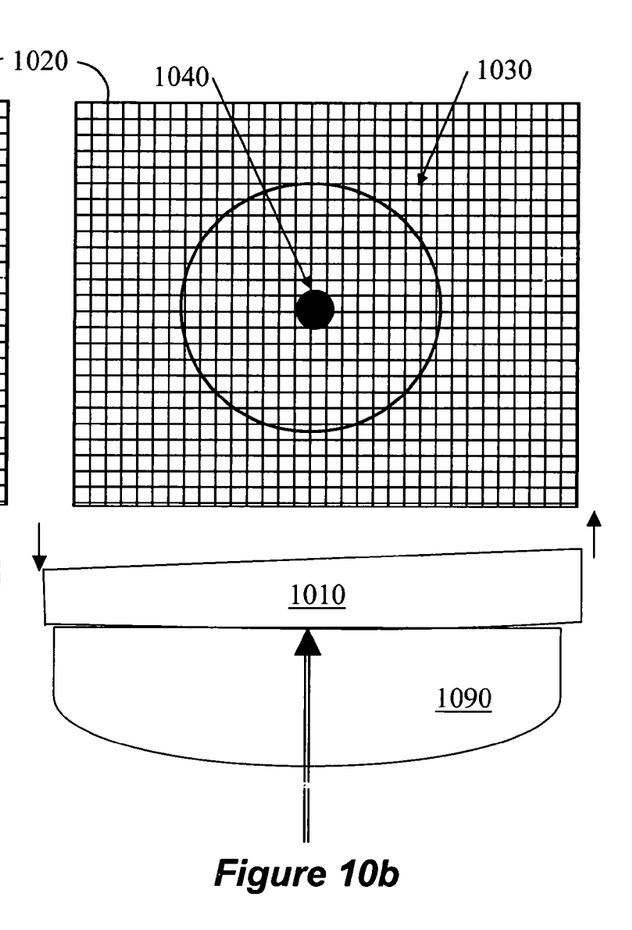

The system of FIG. 8 can be operated and calibrated in the same manner as described above with respect to the embodiment FIG. 2. Another method of leveling the specimen will now be explained with reference to FIG. 9, which is similar to the system shown in FIG. 8. However, this leveling method can also be used with the embodiments of FIGS. 2 and 7. The elements of FIG. 9 that are similar to the elements of FIG. 8 have the same references, except that they are in the 900's range. As shown in FIG. 9, for leveling of the system the specimen is removed and a camera 965 is mounted on the adapter 925 in the same place that the specimen would be mounted. Since this leveling method is particularly useful when a SIL is used, the procedure will be described with reference to a system having a SIL. FIGS. 10A and 10B illustrate the leveling conditions to enable better understanding of the mechanism behind this method. Notably, when the inspection surface 1010 (may be a transparent window in front of a CCD element) is not level, i.e., orthogonal, with respect to the SIL 1090, light collection is possible only with respect to a part T of the bottom surface o the SIL 1090. On the camera 1020 the contact area of the SIL 1090 will show up as circle 1030. However, since the laser beam 1050 passes through the center of the SIL 1090, the laser spot 1040 will show up on camera 1020 as not centered with respect to the circle 1030.

On the other hand, as the adapter 825 is tilted to make the sample/camera orthogonal to the optical axis, much, if not the entire, bottom surface of the SIL can come in contact with the sample, as shown in FIG. 10B. In this case, the laser spot 1040 is shown centered inside the SIL's contact area image circle 1030.

Another embodiment of the invention utilizes the laser in a laser scanning microscope (LSM) configuration. Generally, LSM systems are well known in the art and descriptions of such systems are available in, for example, U.S. Pat. Nos. 5,034,613; 5,936,764; and 6,751,016, which are incorporated herein by reference in their entirety. In LSM, the image is scanned using methods, such as, scanning the object, scanning the optical system in x-y plane, or scanning the input angle of the light beam. For the purpose of the present embodiment, the most effective method is the scanning of the light beam angle, whereby the beam angle determines the spatial position of the focused light spot. For example, the embodiment of FIG. 8 may be used, with mirror 855 and/or mirror 860 acting as scanning mirrors.

For implementing the embodiment using an LSM, the objective may be removed from the optical path, and the laser light reflecting from the sample is imaged. If the surface of the sample that is on the axis of the optical path is orthogonal to the axis of the optical path, an image will be formed at the center of the LSM field of view, as the light will be reflected directly onto the imager. On the other hand, if the surface of the sample is not orthogonal to the axis of the optical path, an image will be form off-center on the LSM field of view. The amount of the off-center image will be directly proportional to the amount of tilt needed to be applied to the sample holder.

While the invention has been described with reference to particular embodiments thereof, it is not limited to those embodiments. Specifically, various variations and modifications may be implemented by those of ordinary skill in the art without departing from the invention's spirit and scope, as defined by the appended claims. Additionally, all of the above-cited prior art references are incorporated herein by reference.

What is claimed is:

1. A system for orthogonal alignment of a specimen to an optical axis of an optical system, comprising:
   a tiltable test bench for placing the specimen thereupon;
   a plurality of lifters coupled to said tiltable test bench and operable to control the leveling of said tiltable test bench;
   optical elements defining an optical path axis, said optical elements comprise a solid immersion lens;
   a light-beam source for illuminating said specimen through said optical elements; and, an imager for imaging said light-beam after reflection from said specimen to thereby provide an indication of leveling position of said tiltable test bench.

2. The system of claim 1, further comprising manual adjustment knobs coupled to said lifters.

3. The system of claim 1, further comprising a plurality of electrical motors each connected to a respective one of said lurality of lifters.

4. The system of claim 3, further comprising a controller coupled to each of said electrical motors.

5. The system of claim 4, further comprising a feedback loop providing a signal from said imager to said controller.

6. The system of claim 1, wherein said light-beam source comprises a laser.

7. The system of claim 2, wherein said light-beam source comprises a laser.

8. The system of claim 3, wherein said light-beam source comprises a laser.

9. The system of claim 1, further comprising a laser scanning microscope (LSM).

10. An integrated system for testing an integrated cfrcuit (IC), comprising:
 a tiltable holder for mounting the IC thereto;
 collection optics comprising a solid immersion lens and a laser scanning microscope (LSM);
 a primary illumination source for illuminating said IC through said collection optics in a navigation mode;
 a light-beam source for illuminating a spot on said IC;
 an imager for imaging said IC using light from said primary source and for imaging said spot on said IC; and
 a photon sensor operable in a detection mode to detect photons emmitted from the IC and generate corresponding electrical signals.

11. A method for leveling a specimen with respect to an optical system having collection optics and an imager, comprising:
 placing said specimen on a tiltable holder;
 operating the imager to image a spot on the specimen through a solid immersions lens;
 noting the imaged location of said spot as reflected onto said imager;
 comparing said imaged location to a reference location; and
 if said imaged location differs from said reference location, tilting said tiltable holder so that the imaged location matches the reference location.

12. A system for alignment of a specimen to an optical axis of an optical system, comprising:
 a tiltable holder bench for placing the specimen thereupon;
 a plurality of lifters coupled to said tiltable holder bench and operable to control the leveling of said tiltable holder bench;
 optical elements defining an optical path axis, wherein said optical elements comprise a solid immersion lens;
 a light-beam source for illuminating said specimen through said optical elements; and,
 an imager for imaging said light-beam after reflection from said specimen to thereby provide an indication of leveling position of said tiltable holder bench.

13. The system of claim 12, further comprising a processor detecting intensity level of the reflection and controlling the tiltable holder to assume a position resulting in highest intensity.

14. The system of claim 12, further comprising a plurality of electrical motors each connected to a respective one of said plurality of lifters.

15. A method for maximizing light collection efficiency in emission testing of a specimen comprising:
 placing a specimen on a tiltable holder bench;
 illuminating the specimen with a light beam at a defined spot;
 measuring intensity of light reflected from the defined spot on the specimen; and
 slanting the tiltable holder bench and specimen while maintaining the illumination at the defined spot until a position is found resulting in the maximum intensity of light reflected from the defined spot.

16. The method of claim 15, wherein the measured intensity is compared to the light beam intensity.

17. The method of claim 15, wherein the light beam is a laser beam.

18. The method of claim 15, wherein the slanting is performed by providing a feedback signal to the tiltable holder bench.

19. The method of claim 18, wherein providing the feedback signal further comprises electronically slanting the tiltable holder bench in response to the measured intensity.

20. The method of claim 15, further comprising placing a solid immersion lens on the specimen.

21. A system for maximizing light collection efficiency in emission testing of a specimen. comprising:
 a tiltable holder bench for placing a specimen thereon;
 a series of optical elements defining an optical path axis;
 a light beam source for illuminating the specimen through the series of optical elements;
 an imager for imaging a light emission intensity;
 a controller for measuring intensity of light beam reflection from the specimen and comparing it to a reference intensity; wherein if the measured intensity is less than the reference intensity, the controller causes the tiltable holder bench to assume another tilt orientation with respect to the optical elements.

22. The system of claim 21, wherein the specimen is an integrated circuit.

23. The system of claim 22, wherein the light beam source is a laser.

24. The system of claim 23, further comprising an imager to detect the light reflected from the specimen.

25. The system of claim 24, further comprising a tilting controller to electronically tilt the tiltable holder bench in response to a comparison by the controller of the light intensity and the reference intensity.

26. system of claim 25, further comprising a feedback loop providing a signal from the controller to the tiltable holder bench.

27. The system of claim 21, wherein the optical elements further comprise a solid immersion lens.

* * * * *